US008278103B2

(12) United States Patent
Damha et al.

(10) Patent No.: US 8,278,103 B2
(45) Date of Patent: *Oct. 2, 2012

(54) OLIGONUCLEOTIDES COMPRISING ALTERNATING SEGMENTS AND USES THEREOF

(75) Inventors: Masad J. Damha, St. Hubert (CA); Michael A. Parniak, Pittsburgh, PA (US)

(73) Assignee: McGill University, Montreal, Quebec (CA)

( * ) Notice: Subject to any disclaimer, the term of this patent is extended or adjusted under 35 U.S.C. 154(b) by 849 days.

This patent is subject to a terminal disclaimer.

(21) Appl. No.: 10/503,120

(22) PCT Filed: Jan. 31, 2003

(86) PCT No.: PCT/CA03/00129
§ 371 (c)(1),
(2), (4) Date: Feb. 17, 2005

(87) PCT Pub. No.: WO03/064441
PCT Pub. Date: Aug. 7, 2003

(65) Prior Publication Data
US 2005/0142535 A1    Jun. 30, 2005

Related U.S. Application Data

(60) Provisional application No. 60/352,873, filed on Feb. 1, 2002.

(51) Int. Cl.
*C12N 5/00* (2006.01)
*C12N 5/02* (2006.01)
*C12N 15/11* (2006.01)
*C07H 21/04* (2006.01)

(52) U.S. Cl. ............. 435/375; 514/44 A; 536/23.2; 536/24.5

(58) Field of Classification Search .......... None
See application file for complete search history.

(56) References Cited

U.S. PATENT DOCUMENTS

| | | | |
|---|---|---|---|
| 4,806,463 A | 2/1989 | Goodchild et al. | |
| 5,004,810 A | 4/1991 | Draper | |
| 5,087,617 A | 2/1992 | Smith | |
| 5,098,890 A | 3/1992 | Gewirtz | |
| 5,135,917 A | 8/1992 | Burch | |
| 5,166,195 A | 11/1992 | Ecker | |
| 5,194,428 A | 3/1993 | Agrawal et al. | |
| 5,264,423 A | 11/1993 | Cohen et al. | |
| 5,276,019 A | 1/1994 | Cohen et al. | |
| 5,286,717 A | 2/1994 | Cohen et al. | |
| 5,539,082 A | 7/1996 | Nielsen et al. | |
| 5,576,208 A * | 11/1996 | Monia et al. | 435/375 |
| 5,932,435 A | 8/1999 | Atkins et al. | |
| 5,955,589 A * | 9/1999 | Cook et al. | 536/23.1 |
| 6,326,358 B1 | 12/2001 | Manoharan | |

FOREIGN PATENT DOCUMENTS

| | | |
|---|---|---|
| WO | WO 99150409 | 10/1999 |
| WO | WO 99167378 | 12/1999 |
| WO | WO 02/20773 | 3/2002 |

OTHER PUBLICATIONS

Damha, et al. (1998) Hybrids of RNA and Arabinonucleic Acids (ANA and 2'F-ANA) Are Substrates of Ribonuclease H, J. Am. Chem. Soc., v.120: 12976-12977.*
Damha, et al. (1998) Hybrids of RNA and Arabinonucleic Acids (ANA and 2'F-ANA) Are Substrates of Ribonuclease H. J. Am.Chem. Soc., v.120:12976-7.*
Kois, et al. (1993) Oligodeoxynucleotides Containing 2'-Fluoro-Arabino-Nucleotide and C-Nucleotide. Nucleic Acids Symposium Series No. 29:215-6.*
Nielsen, P. et al.; Incorporation of (R)- and (S)-3',4'-seco-thymidine into oligodeoxynucleotides: hybridization properties and enzymatic stability, Nucleic Acids Research, 22(5):703-710 (1994).
Cook, Dan P., "Making Drugs Out of Oligonucleotides: A Brief Review and Perspective," Nucleosides, Nucleotides and Nucleic Acids, 18(6):1141-1162 (1999).
Hogrefe, Holly H. et al., "Kinetic Analysis of *Escherichia coli* RNase H Using DNA-RNA-DNA/DNA Substrates," The Journal of Biological Chemistry, 265(10):5561-5566 (1990).
Inoue, Hideo et al., "Sequence-dependent hydrolysis of RNA using modified oligonucleotide splints and RNase H," FEBS Letters, 215(2):327-330 (1987).
Shibahara, Susumu et al., "Site-directed cleavage of RNA," Nucleic Acids Research, 15(11):4403-4415 (1987).
Uhlmann, Eugen et al., "Antisense Oligonucleotides: A New Therapeutic Principle," Chemical Reviews, 90 (4):544-584 (1990).
Crooke, S. et al., Biochem J., 312:599-608 (1995). "Kinetic characteristics of *Escherichia coli* RNase H1: cleavage of various antisense oligonucleotide-RNA duplexes."
Cummins, L. et al., Biochemistry, 35:8734-8741 (1996). "Biochemical and Physicochemical Properties of Phosphorodithioate NDA."
Iwai, S., J. Mol. Biol., 263:699-706 (1996). "Interaction of the Basic Protrusion of *Escherichia coli* Ribonuclease HI with its Substrate."
Kanaya, S. et al., The Journal of Biological Chemistry, 266(18):11621-11627 (1991). "Importance of the Positive Charge Cluster in *Escherichia coli* Ribonuclease HI for the Effective Binding of the Substrate."
Lima, W.F., Biochemistry, 36:390-398 (1997). "Binding Affinity and Specificity of *Escherichia coli* RNase H1: Impact on the Kinetics of Catalysis of Antisense Oligonucleotide-RNA Hybrids."

(Continued)

*Primary Examiner* — Jennifer Pitrak McDonald
(74) *Attorney, Agent, or Firm* — Nixon Peabody LLP; David S. Resnick; Leena H. Karttunen Contarino

(57) ABSTRACT

The invention relates to oligonucleosides having alternating segments of sugar-modified nucleosides and 2'-deoxynucleosides, and uses thereof. The invention further relates to oligonucleotides having alternating segments of sugar-modified nucleotides and 2'-deoxynucleotides, and uses thereof. Such uses include the preparation of antisense oligonucleotides and their use for the prevention or depletion of function of a target nucleic acid of interest, such as an RNA, in a system. Accordingly, an oligonucleotide of the invention is useful for therapeutic, analytical and diagnostic methods and uses, as well as a component of compositions and commercial packages corresponding to such methods and uses.

23 Claims, 3 Drawing Sheets

OTHER PUBLICATIONS

Manoharan, M., Biochimica et Biophysica Acta, 1489:117-130 (1999). "2'-Carbohydrate modifications in antisense oligonucleotide therapy: importance of conformation, configuration and conjugation."

Monia, B.P. et al., The Journal of Biological Chemistry, 268(19):14514-14522 (1993). "Evaluation of 2'-Modified Oligonucleotides Containing 2'-Deoxy Gaps as Antisense Inhibitors of Gene Expression."

Walder, R.Y. and Walder, J.A., Proc. Natl. Acad. Sci. USA, 85:5011-5015 (1988). "Role of RNase H in hybrid-arrested translation by antisense oligonucleotides."

Wu, H. et al., The Journal of Biological Chemistry, 274(40):28270-28278 (1999). "Properties of Cloned and Expressed Human RNase H1."

Wu, H. et al., The Journal of Biological Chemistry, 276:23547-23553 (2001). "Investigating the Structure of Human RNase H1 by Site-directed Mutagenesis."

Zamaratski, E. et al., J. Biochem. Biophys. Methods, 48:189-208 (2001). "A critical survey of the structure-function of the antisense oligo/RNA heteroduplex as substrate for RNase H."

Nakamura, H. et al. "How does RNase H recognize a DNA.RNA hybrid?" Proc. Natl. Acad. Sci. USA 88 (24):11535-9, 1991.

Trempe, J-F et al. "NMR solution structure of an oligonucleotide hairpin with a 2'F-ANA/RNA stem: implications for RNase H specificity toward DNA/RNA hybrid duplexes." J Am Chem Soc. 123(21):4896-903, 2001.

Denisov A.Y. et al., "Solution structure of an arabinonucleic acid (ANA)/RNA duplex in a chimeric hairpin: comparison with 2'-fluoro-ANA/RNA and DNA/RNA hybrids." Nucleic Acids Res 29(21):4284-93, 2001.

Nielsen et al., "Sequence-selective recognition of DNA by strand displacement with a thymine-substituted polyamide." Science. 254(5037):1497-500, 1991.

Wilds, C.J. & Damha, M.J. "2'-Deoxy-2'-fluoro-beta-D-arabinonucleosides and oligonucleotides (2'F-ANA): synthesis and physicochemical studies." Nucleic Acids Res. 28(18):3625-35, 2000.

Gutierrez, A. J. et al., "Antisense gene inhibition by C-5-substituted deoxyuridine-containing oligodeoxynucleotides." Biochemistry. 36(4):743-8, 1997.

Flanagan, W. M. et al., "A cytosine analog that confers enhanced potency to antisense oligonucleotides." Proc Natl Acad Sci U S A. 96(7):3513-8, 1999.

Damha, M-J et al., "Antisense L/D-oligodeoxynucleotide chimeras: nuclease stability, base-pairing properties, and activity at directing ribonuclease H." Biochemistry. 33(25):7877-85, 1994.

Tazawa, I. et al., "L'adenylyl-(3'-5')-L-adenosine and L-adenylyl-(2'-5')-L-adenosine." Biochemistry. 9(18):3499-514, 1970.

Agrawal, S. and Kandimalla, ER., "Antisense therapeutics: is it as simple as complementary base recognition?" Mol Med Today. 6(2):72-81, 2000.

Jen, KY and Gewirtz, AM. "Suppression of gene expression by targeted disruption of messenger RNA: available options and current strategies." Stem Cells. 18(5):307-19, 2000.

Wilds, CJ and Damha, MJ. "Duplex recognition by oligonucleotides containing 2'-deoxy-2'-fluoro-D-arabinose and 2'-deoxy-2'-fluoro-D-ribose. Intermolecular 2'-OH-phosphate contacts versus sugar puckering in the stabilization of triple-helical complexes." Bioconjug Chem. 10(2):299-305, 1999.

Manoharan, M. "2'-carbohydrate modifications in antisense oligonucleotide therapy: importance of conformation, configuration and conjugation." Biochim Biophys Acta. 1489(1):117-30, 1999.

Fedoroff, OY, et al., "Structure of a DNA:RNA hybrid duplex. Why RNase H does not cleave pure RNA." J Mol Biol. 233(3):509-23, 1993.

Kandimalla, ER et al., "Mixed backbone antisense oligonucleotides: design, biochemical and biological properties of oligonucleotides containing 2'-5'-ribo- and 3'-5'-deoxyribonucleotide segments." Nucleic Acids Res. 25(2):370-8, 1997.

Oda, Y. et al., "Binding of nucleic acids to E. coli RNase HI observed by NMR and CD spectroscopy." Nucleic Acids Res. 21(20):4690-5, 1993.

Venkateswarlu, D, et al., "Structural properties of DNA:RNA duplexes containing 2'-O-methyl and 2'-S-methyl substitutions: a molecular dynamics investigation." Nucleic Acids Res. 27(10):2189-95, 1999.

Hausen, P. and Stein, H., "Ribonuclease H: an Enzyme Degrading the RNA Moiety of DNA-RNA Hybrids." Eur. J. Biochem. 14:278-283, 1970.

Venkateswarlu, D. and Ferguson, D. M., "Effects of C2'-Substitution on Arabinonucleic Acid Structure and Conformation." J. Am. Chem. Soc. 121:5609-10, 1999.

Petersen, M. et al., "alpha-L-LNA (alpha-I-ribo Configured Locked Nucleic Acid) Recognition of RNA. A Study by NMR Spectroscopy and Molecular Dynamics Simulations." J. Am. Chem. Soc. 123:7431-2, 2001.

Wang, J. et al., "Cyclohexene Nucleic Acids (CeNA): Serum Stable Oligonucleotides that Activate RNase H and Increase Duplex Stability with Complementary RNA." J. Am. Chem. Soc. 122:8595-8602, 2000.

Elzagheid, M. I. et al., "Synthesis of Protected 2'-Deoxy-2'-fluoro-beta-D-arabinonucleosides." Current Protocols in Nuclear Acid Chemistry, Supplement 10, 1.7.1-1.7.19, Beaucage, S.L., Bergstrom, D.E., Gli, G.D., (eds.), 2002.

Viazovkina, E., et al., "Solid-Phase Synthesis of 2'-Deoxy-2'-fluoro-beta-D-Oligoarabinonucleotides (2'F-ANA) and Their Phosphorothioate Derivatives." Current Protocols in Nuclear Acid Chemistry, Supplement 10, 4.15.1-4.15.22, Beaucage, S.L., Bergstrom, D.E., Gli, G.D., (eds.), 2002.

Wu, A. F. and Chargaff, E., "L-Uridine: Synthesis and Behavior as Enzyme Substrate." Biochemistry 63:1222-1226, 1969.

Giannaris, P. A. and Damha, M. J., "Hybridization properties of oligoarabinonucleotides." Can. J. Chem. 72:909-18, 1994.

* cited by examiner

A)

B)

SEQUENCE LISTING

```
<160> NUMBER OF SEQ ID NOS: 22

<210> SEQ ID NO 1
<211> LENGTH: 18
<212> TYPE: DNA
<213> ORGANISM: Artificial
<220> FEATURE:
<223> OTHER INFORMATION: Oligonucleotide

<400> SEQUENCE: 1
tttttttttt tttttttt                                              18

<210> SEQ ID NO 2
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(18)
<223> OTHER INFORMATION: Residues 1 to 18 are 2'-deoxy-2'-
      fluoroarabinothymidine

<400> SEQUENCE: 2
nnnnnnnnnn nnnnnnnn                                              18

<210> SEQ ID NO 3
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(17)
<223> OTHER INFORMATION: Residues 1, 3, 5, 7, 9, 11, 13, 15, 17 are
      2'-deoxy-2'-fluoroarabinothymidine
<220> FEATURE:
<221> NAME/KEY: misc_feature
<222> LOCATION: (1)..(17)
<223> OTHER INFORMATION: Residues 1, 3, 5, 7, 9, 11, 13, 15 and 17 are
      2'-deoxy-2'-fluoroarabinothymidine

<400> SEQUENCE: 3
ntntntntnt ntntntnt                                              18

<210> SEQ ID NO 4
<211> LENGTH: 18
```

```
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(18)
<223> OTHER INFORMATION: Residues 1, 2, 5, 6, 9, 10, 13, 14, 17 and 18
      are 2'-deoxy-2'-fluoroarabinothymidine

<400> SEQUENCE: 4
nnttnnttnn ttnnttnn                                                 18

<210> SEQ ID NO 5
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(15)
<223> OTHER INFORMATION: Residues 1-3, 7-9 and 13-15 are
      2'-deoxy-2'-fluoroarabinothymidine

<400> SEQUENCE: 5
nnntttnnnt tnnnttt                                                  18

<210> SEQ ID NO 6
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(18)
<223> OTHER INFORMATION: Residues 1-4, 8-11 and 15-18 are 2'-deoxy-2'-
      fluoroarabinothymidine

<400> SEQUENCE: 6
nnnntttnnn ntttnnnn                                                 18

<210> SEQ ID NO 7
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(18)
<223> OTHER INFORMATION: Residues 1-6 and 13-18 are 2'-deoxy-2'-
      fluoroarabinothymidine

<400> SEQUENCE: 7
nnnnnntttt ttnnnnnn                                                 18

<210> SEQ ID NO 8
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(17)
<223> OTHER INFORMATION: Residues 1, 3, 5, 7, 9, 11, 13, 15 and 17 are
      2'-O-methyl-D-uridine

<400> SEQUENCE: 8
```

```
utututut utututut                                                          18

<210> SEQ ID NO 9
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(15)
<223> OTHER INFORMATION: Residues 1-3, 7-9, and 13-15 are 2'-O-methyl-
      D-uridine

<400> SEQUENCE: 9
uuutttuuut ttuuuttt                                                        18

<210> SEQ ID NO 10
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(18)
<223> OTHER INFORMATION: Residues 1-6 and 13-18 are 2'-O-methyl-
      D-uridine

<400> SEQUENCE: 10
uuuuuutttt ttuuuuuu                                                        18

<210> SEQ ID NO 11
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(18)
<223> OTHER INFORMATION: Residues 1-18 are linked by phosphorothioate
      linkages

<400> SEQUENCE: 11
atatccttgt cgtatccc                                                        18

<210> SEQ ID NO 12
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(15)
<223> OTHER INFORMATION: Residues 2, 7, 8, 13 and 15 are 2'-deoxy-2'-
      fluoroarabinothymidine; residues 1, 3 and 14 are 2'-deoxy-2'-
      fluoroarabinoadenosine; residue 9 is 2'-deoxy-2'-
      fluoroarabinoguanosine
<220> FEATURE:
<221> NAME/KEY: misc_feature
<222> LOCATION: (1)..(18)
<223> OTHER INFORMATION: Residues 1-18 are linked by phosphorothioate
      linkages

<400> SEQUENCE: 12
nnntccnnnt cgnnnccc                                                        18

<210> SEQ ID NO 13
<211> LENGTH: 18
```

```
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(8)
<223> OTHER INFORMATION: Residues 1 and 3 are 2'-deoxy-2'-
      fluoroarabinothymidine; residues 2, 4, 7 and 8 are 2'-deoxy-2'-
      fluoroarabinoadenosine; residues 5 and 6 are 2'-deoxy-2'-
      fluoroarabinocytidine
<220> FEATURE:
<221> NAME/KEY: misc_feature
<222> LOCATION: (1)..(18)
<223> OTHER INFORMATION: Residues 1-18 are linked by phosphorothioate
      linkages

<400> SEQUENCE: 13
nnnnnnnngt cgtatccc                                                       18

<210> SEQ ID NO 14
<211> LENGTH: 17
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(17)
<223> OTHER INFORMATION: Residues 2, 8 and 13 are 2'-deoxy-2'-
      fluoroarabinothymidine; residues 3 and 5 are 2'-deoxy-2'-
      fluoroarabinoadenosine; residues 12 and 16-18 are 2'-deoxy-2'-
      fluoroarabinocytidine
<220> FEATURE:
<221> NAME/KEY: misc_feature
<222> LOCATION: (1)..(17)
<223> OTHER INFORMATION: Residues 1-17 are linked by phosphorothioate
      linkages

<400> SEQUENCE: 14
nngctnnnca nnngann                                                        17

<210> SEQ ID NO 15
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(18)
<223> OTHER INFORMATION: Residues 1 and 3 are 2'-O-methyl-D-adenosine;
      residues 2, 4 and 15 are 2'-O-methyl-D-uridine; residues 16-18 are
      2'-O-methyl-D-cytidine; residues 7 and 8 are 2'-deoxy-2'-
      fluoroarabinothymidine; residue 11 is 2'-deoxy-2'-
      fluoroarabinocytidine; residue 12 is 2'-deoxy-2'-
      fluoroarabinoguanosine
<220> FEATURE:
<221> NAME/KEY: misc_feature
<222> LOCATION: (1)..(18)
<223> OTHER INFORMATION: Residues 1-18 are linked by phosphorothioate
      linkages

<400> SEQUENCE: 15
auauccnngt nntauccc                                                       18

<210> SEQ ID NO 16
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
```

```
<222> LOCATION: (1)..(18)
<223> OTHER INFORMATION: Residues 1 and 3 are 2'-O-methyl-D-adenosine;
      residues 2, 4 and 15 are 2'-O-methyl-D-uridine; residues 16-18 are
      2'-O-methyl-D-cytidine; residue 7 is 2'-deoxy-2'-
      fluoroarabinothymidine; residues 5, 6 and 11 are 2'-deoxy-2'-
      fluoroarabinocytidine; residue 12 is 2'-deoxy-2'-
      fluoroarabinoguanosine
<220> FEATURE:
<221> NAME/KEY: misc_feature
<222> LOCATION: (1)..(18)
<223> OTHER INFORMATION: Residues 1-18 are linked by phosphorothioate
      linkages

<400> SEQUENCE: 16
auaunnntgt nntauccc                                               18

<210> SEQ ID NO 17
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(18)
<223> OTHER INFORMATION: Residues 1 and 3 are 2'-O-methyl-D-adenosine;
      residues 2, 4 and 15 are 2'-O-methyl-D-uridine; residues 16-18 are
      2'-O-methyl-D-cytidine; residues 7 and 8 are 2'-deoxy-2'-
      fluoroarabinothymidine; residues 5 and 6 are 2'-deoxy-2'-
      fluoroarabinocytidine; residue 9 is 2'-deoxy-2'-
      fluoroarabinoguanosine
<220> FEATURE:
<221> NAME/KEY: misc_feature
<222> LOCATION: (1)..(18)
<223> OTHER INFORMATION: Residues 1-18 are linked by phosphorothioate
      linkages

<400> SEQUENCE: 17
auaunnnnnt cgtauccc                                               18

<210> SEQ ID NO 18
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(18)
<223> OTHER INFORMATION: Residues 1 and 3 are 2'-O-methyl-D-adenosine;
      residues 2, 4 and 15 are 2'-O-methyl-D-uridine; residues 16-18 are
      2'-O-methyl-D-cytidine; residues 7, 8, 10 and 13 are 2'-deoxy-2'-
      fluoroarabinothymidine; residue 14 is 2'-deoxy-2'-
      fluoroarabinoadenosine; residues 5, 6 and 11 are 2'-deoxy-2'-
      fluoroarabinocytidine; residues 9 and 12 are 2'-deoxy-2'-
      fluoroarabinoguanosine
<220> FEATURE:
<221> NAME/KEY: misc_feature
<222> LOCATION: (1)..(18)
<223> OTHER INFORMATION: Residues 1-18 are linked by phosphorothioate
      linkages

<400> SEQUENCE: 18
auaunnnnnn nnnnuccc                                               18

<210> SEQ ID NO 19
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(18)
```

```
<223> OTHER INFORMATION: Residues 1, 3, 4 and 16 are 2'-O-methyl-D-
      adenosine; residue 2 is 2'-O-methyl-D-uridine; residues 17-19 are
      2'-O-methyl-D-cytidine; residues 9 and 12 are 2'-deoxy-2'-
      fluoroarabinothymidine; residue 14 is 2'-deoxy-2'-
      fluoroarabinoadenosine
<220> FEATURE:
<221> NAME/KEY: misc_feature
<222> LOCATION: (1)..(18)
<223> OTHER INFORMATION: Residues 1-18 are linked by phosphorothioate
      linkages

<400> SEQUENCE: 19
auaaccttnt cntnaccc                                                18

<210> SEQ ID NO 20
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(18)
<223> OTHER INFORMATION: Residues 1 and 3 are 2'-O-methyl-D-adenosine;
      residues 2, 4 and 15 are 2'-O-methyl-D-uridine; residues 16-18 are
      2'-O-methyl-D-cytidine
<220> FEATURE:
<221> NAME/KEY: misc_feature
<222> LOCATION: (1)..(18)
<223> OTHER INFORMATION: Residues 1-18 are linked by phosphorothioate
      linkages

<400> SEQUENCE: 20
auauccttgt cgtauccc                                                18

<210> SEQ ID NO 21
<211> LENGTH: 18
<212> TYPE: RNA
<213> ORGANISM: Artificial
<220> FEATURE:
<223> OTHER INFORMATION: Target RNA oligonucleotide

<400> SEQUENCE: 21
aaaaaaaaaa aaaaaaaa                                                18

<210> SEQ ID NO 22
<211> LENGTH: 22
<212> TYPE: RNA
<213> ORGANISM: Artificial
<220> FEATURE:
<223> OTHER INFORMATION: Target RNA oligonucleotide

<400> SEQUENCE: 22
aagggauacg acaaggauau aa                                           22
```

OLIGONUCLEOTIDES COMPRISING ALTERNATING SEGMENTS AND USES THEREOF

CROSS-REFERENCE TO RELATED APPLICATIONS

This application is a 371 National Phase Entry Application of co-pending International Application PCT/CA03/00129, filed Jan. 31, 2003, which designated the U.S. and which claims the benefit under 35 U.S.C. §119(e) of U.S. Provisional Application 60/352,873, filed Feb. 1, 2002.

FIELD OF THE INVENTION

The invention relates to oligonucleosides and oligonucleotides and uses thereof, and particularly relates to modified oligonucleosides and oligonucleotides and uses thereof.

BACKGROUND OF THE INVENTION

Oligonucleotides are utilized for a variety of biotechnological applications, based on their ability to confer specificity by virtue of their sequence composition. Given, for example, their ability to be designed to target a protein-encoding molecule, such as RNA, a particular use of oligonucleotides is in antisense technology.

Antisense Oligonucleotides (AONs)

Antisense oligonucleotides (AONs) have attracted considerable interest in the biotechnology sector, and have exceptional potential for use in therapeutic strategies against a range of human diseases. The formation of a duplex between the AON and its complementary sequence on its target (usually messenger RNA [mRNA]) prevents the translation of such RNA, in part by "translation arrest" (via duplex formation between the AON and the target RNA, thus inhibiting/preventing complete translation by physically or sterically blocking the translational machinery) but more importantly by eliciting degradation of the targeted RNA through the action of ribonuclease H(RNase H), a ubiquitous and endogenous cellular enzyme that specifically degrades the RNA strand in the AON/RNA duplex.

Since the natural substrate of RNase H is a DNA/RNA heteroduplex, DNA has been utilized for antisense technology. However, as serum and intracellular nucleases rapidly degrade AONs with phosphodiester (PDE) linkages, AON consisting of PDE-DNA have had limited utility in such systems. DNA with phosphorothioate linkages (PS-DNA) can induce RNase H degradation of the targeted RNA, and is resistant to degradation by serum and cellular nucleases, however, it forms weaker duplexes with the target RNA compared to PDE-DNA.

RNase H

RNase H selectively degrades the RNA strand of a DNA/RNA heteroduplex (Hausen, P.; Stein, H. *Eur. J. Biochem.* 1970, 14, 279). Studies with eukaryotic cell extracts containing RNase H suggest that both prokaryotic and eukaryotic enzymes exhibit similar RNA-cleavage properties (Monia et al. *J. Biol. Chem.* 1993, 268, 14514; Crooke et al. *Biochem J.* 1995, 312, 599; Lima, W. F.; Crooke, S.T. *Biochemistry* 1997, 36, 390). *E. coli* RNase H1 is thought to bind to the minor groove of the DNA/RNA double helix and to cleave the RNA by both endonuclease and processive 3'-to-5' exonuclease activities (Nakamura, H. et al. *Proc. Natl. Acad. Sci. USA* 1991, 88, 11535; Fedoroff, O.Y. et al., *J. Mol. Biol.* 1993, 233, 509). The efficiency of RNase H degradation displays minimal sequence dependence and, as mentioned above, is quite sensitive to chemical changes in the antisense oligonucleotide.

There is therefore a need for an improved oligonucleotide, to address one or more of the limitations noted above.

SUMMARY OF THE INVENTION

According to a first aspect, the invention provides an oligonucleoside comprising alternating segments of sugar-modified nucleosides and 2'-deoxynucleosides, wherein the segments or units each independently comprise at least one sugar-modified nucleoside or 2'-deoxynucleoside, respectively. For example, the oligonucleoside comprises alternating first and second segments, wherein the first segment comprises at least one sugar-modified nucleoside, and wherein the second segment comprises at least one 2'-deoxynucleoside. In embodiments, the oligonucleoside comprises at least 2 of each of the first and second segments thereby comprising at least 4 alternating segments.

In an embodiment, the oligonucleoside comprises an internucleoside linkage comprising a phosphate, thereby being an oligonucleotide. In embodiments the sugar-modified nucleosides and/or 2'-deoxynucleosides comprise a phosphate, thereby being sugar-modified nucleotides and/or 2'-deoxynucleotides.

In an embodiment, the invention provides an oligonucleotide comprising alternating segments or units of arabinonucleotides and 2'-deoxynucleotides, wherein said segments or units each independently comprise at least one arabinonucleotide or 2'-deoxynucleotide, respectively. In an embodiment, the oligonucleotide comprises at least 2 arabinonucleotide segments and at least 2 2'-deoxynucleotide segments thereby having at least 4 of the alternating units.

In an embodiment, the sugar-modified oligonucleotide is capable of adopting a DNA-like conformation. In an embodiment, the sugar-modified nucleotide is selected from the group consisting of arabinonucleotides, alpha-L-locked nucleic acids, cyclohexene nucleic acids, and ribonucleotides lacking an electronegative 2'-oxygen atom. In an embodiment, the ribonucleotides lacking an electronegative 2'-oxygen atom are selected from the group consisting of 2'-alkyl-D-ribose and 2'-SCH$_3$-D-ribose.

In an embodiment, the segments each independently comprise about 1 to about 6 arabinonucleotides or 2'-deoxynucleotides. In further embodiments, the segments each independently comprise about 2 to about 5 or about 3 to about 4 arabinonucleotides or 2'-deoxynucleotides. In a further embodiment, the segments each independently comprise about 3 arabinonucleotides or 2'-deoxynucleotides.

In an embodiment, the above-mentioned oligonucleotide has a structure selected from the group consisting of:

| | | |
|---|---|---|
| a) | $(A_x - D_y)_n$ | I |
| b) | $(D_y - A_x)_n$ | II |
| c) | $(A_x - D_y)_m - A_x - D_y - A_x$ | III |
| d) | $(D_y - A_x)_m - D_y - A_x - D_y$ | IV | wherein each of m, x and y are each independently an integer greater than or equal to 1, n is an integer greater than or equal to 2, A is an sugar-modified nucleotide and D is a 2'-deoxyribonucleotide.

In an embodiment, the above-mentioned sugar-modified nucleotide comprises a 2' substituent selected from the group consisting of fluorine, hydroxyl, amino, cyano, azido, —CH=CH$_2$, —C≡CH, alkyl, functionalized alkyl, alkoxy and functionalized alkoxy groups. In an embodiment, the alkyl group is a lower alkyl group. In an embodiment, the lower alkyl group is selected from the group consisting of methyl, ethyl and propyl groups. In an embodiment, the functionalized alkyl group is selected from the group consisting of methylamino, ethylamino and propylamino groups. In an embodiment, the alkoxy group is selected from the group consisting of methoxy, ethoxy and propoxy groups. In an embodiment, the functionalized alkoxy group is —O(CH$_2$)$_q$—R, wherein q=2, 3 or 4 and —R is selected from the group consisting of —NH$_2$, —OCH$_3$, and —OCH$_2$CH$_3$ groups.

In an embodiment, the sugar-modified nucleotide is an arabinonucleotide. In a further embodiment, the 2' substituent is fluorine and the arabinonucleotide is a 2'-fluoroarabinonucleotide (2'F-ANA; also abbreviated "FANA").

In an embodiment, the above-mentioned oligonucleotide comprises one or more internucleotide linkages selected from the group consisting of:
a) phosphodiester;
b) phosphotriester;
c) phosphorothioate;
d) phosphorodithioate;
e) Rp-phosphorothioate;
f) Sp-phosphorothioate;
g) boranophosphate;
h) methylene (methylimino) (3'CH$_2$—N(CH$_3$)—O5');
i) 3'-thioformacetal (3'S—CH2-O5')
j) amide (3'CH$_2$—C(O)NH-5');
k) methylphosphonate;
l) phosphoramidate (3'-OP(O$_2$)—N5'); and
m) any combination of (a) to (1).

In an embodiment, the above-mentioned oligonucleotide consists of about 30 or fewer nucleotides, in a further embodiment, about 8 to about 25 nucleotides, in yet a further embodiment, about 18 nucleotides.

In an embodiment, the above-mentioned oligonucleotide has structure I wherein x=1, y=1 and n=9, thereby having a structure:

A-D-A-D-A-D-A-D-A-D-A-D-A-D-A-D-A-D.

In an embodiment, the above-mentioned oligonucleotide has structure II wherein x=1, y=1 and n=9, thereby having a structure:

D-A-D-A-D-A-D-A-D-A-D-A-D-A-D-A-D-A.

In an embodiment, the above-mentioned oligonucleotide has structure III wherein x=2, y=2 and m=3, thereby having a structure:

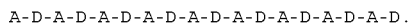
A-A-D-D-A-A-D-D-A-A-D-D-A-A-D-D-A-A.

In an embodiment, the above-mentioned oligonucleotide has structure IV wherein x=2, y=2 and m=3, thereby having a structure:

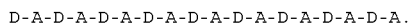
D-D-A-A-D-D-A-A-D-D-A-A-D-D-A-A-D-D.

In an embodiment, the above-mentioned oligonucleotide has structure I wherein x=3, y=3 and n=3, thereby having a structure:

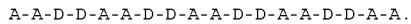
A-A-A-D-D-D-A-A-A-D-D-D-A-A-A-D-D-D.

In an embodiment, the above-mentioned oligonucleotide has structure II wherein x=3, y=3 and n=3, thereby having a structure:

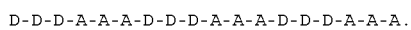
D-D-D-A-A-A-D-D-D-A-A-A-D-D-D-A-A-A.

In an embodiment, the above-mentioned oligonucleotide has structure III wherein x=4, y=3 and m=1, thereby having a structure:

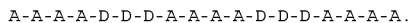
A-A-A-A-D-D-D-A-A-A-A-D-D-D-A-A-A-A.

In an embodiment, the above-mentioned oligonucleotide has said structure IV wherein x=4, y=3 and m=1, thereby having a structure:

D-D-D-D-A-A-A-D-D-D-D-A-A-A-D-D-D-D.

In an embodiment, the above-mentioned oligonucleoside further comprises a third segment comprising a modified nucleoside, wherein said third segment is adjacent to (a) the 5' end of said alternating first and second segments, (b) the 3' end of said alternating first and second segments, or (c) both (a) and (b).

In an embodiment, the above-mentioned oligonucleotide further comprises a third segment comprising a modified nucleotide, wherein said third segment is adjacent to (a) the 5' end of said alternating first and second segments, (b) the 3' end of said alternating first and second segments, or (c) both (a) and (b). In an embodiment, the modified nucleotide is a modified ribonucleotide. In an embodiment, the modified ribonucleotide comprises a modification at its 2' position. In an embodiment, the 2' modification is selected from the group consisting of methoxy, methoxyethyl, fluoro and propylamino groups.

In an embodiment, the above-mentioned oligonucleotide is antisense to a target RNA.

The invention further provides a method of preventing or decreasing translation, reverse transcription and/or replication of a target RNA in a system, said method comprising contacting said target RNA with the above-mentioned oligonucleotide. In an embodiment, the system is selected from the group consisting of a cell, tissue or subject. In an embodiment, the cell, tissue or subject is a mammalian cell, tissue or subject, in a further embodiment, a human cell, tissue or subject.

The invention further provides a method of inducing RNase H-mediated cleavage of a target RNA in a system, the method comprising contacting the target RNA with the above-mentioned oligonucleotide. In an embodiment, the RNase H-mediated cleavage is effected by RNase H activity associated with a reverse transcriptase of a virus. In an embodiment, the virus is a human pathogenic virus, in a further embodiment, the virus is selected from the group consisting of HIV (e.g. HIV-1 and HIV-2) and hepadnaviruses (e.g. hepatitis B virus). In an embodiment, the RNase H-mediated cleavage is effected by RNase H activity associated with an RNase H enzyme of prokaryotic or eukaryotic origin. In an embodiment, the eukaryotic RNase H is a mammalian RNase H, in a further embodiment, a human RNase H (e.g. RNase H1 and RNase H2).

The invention further provides a method of preventing or decreasing translation, reverse transcription and/or replication of a target RNA in a system, and/or for detecting the presence of a target RNA in a system and/or validating a gene target in a system, said method comprising:
a) contacting the target RNA with the above-mentioned oligonucleotide; and
b) allowing RNase H cleavage of the target RNA.

The invention further provides a method of effecting a process selected from the group consisting of:
(a) inducing RNase H-mediated cleavage of a target RNA in a system;
(b) preventing or decreasing translation of a target RNA in a system;
(c) preventing or decreasing reverse transcription of a target RNA in a system;
(d) preventing or decreasing replication of a target RNA in a system
(e) detecting the presence of a target RNA in a system
(f) validating a gene target corresponding to a target RNA in a system;
(g) preventing or treating a disease related to a target RNA in a system; and
(h) any combination of (a) to (g);
said method comprising contacting said target RNA with the above-mentioned oligonucleotide.

The invention further provides a method of effecting a process selected from the group consisting of:
(a) inducing RNase H-mediated cleavage of a target RNA in a system;
(b) preventing or decreasing translation of a target RNA in a system;
(c) preventing or decreasing reverse transcription of a target RNA in a system;
(d) preventing or decreasing replication of a target RNA in a system
(e) detecting the presence of a target RNA in a system
(f) validating a gene target corresponding to a target RNA in a system;
(g) preventing or treating a disease related to a target RNA in a system; and
(h) any combination of (a) to (g);
said method comprising introducing the above-mentioned oligonucleotide into said system.

The invention further provides a use of the above-mentioned oligonucleotide for a medical or research use. In embodiments, the medical or research use is selected from the group consisting of:
(a) inducing RNase H-mediated cleavage of a target RNA in a system;
(b) preventing or decreasing translation of a target RNA in a system;
(c) preventing or decreasing reverse transcription of a target RNA in a system;
(d) preventing or decreasing replication of a target RNA in a system
(e) detecting the presence of a target RNA in a system
(f) validating a gene target in a system;
(g) preventing or treating a disease related to a target RNA in a system; and
(h) any combination of (a) to (g).

The invention further provides a use of the above-mentioned oligonucleotide for the preparation of a medicament. In an embodiment the medicament is for a use selected from the group consisting of:
(a) inducing RNase H-mediated cleavage of a target RNA in a system;
(b) preventing or decreasing translation of a target RNA in a system;
(c) preventing or decreasing reverse transcription of a target RNA in a system;
(d) preventing or decreasing replication of a target RNA in a system;
(e) detecting the presence of a target RNA in a system;
(f) validating a gene target in a system;
(g) preventing or treating a disease related to a target RNA in a system; and
(h) any combination of (a) to (g).

The invention further provides a composition comprising the above-mentioned oligonucleotide in admixture with a pharmaceutically acceptable carrier. In an embodiment, the composition is for a use selected from the group consisting of:
(a) inducing RNase H-mediated cleavage of a target RNA in a system;
(b) preventing or decreasing translation of a target RNA in a system;
(c) preventing or decreasing reverse transcription of a target RNA in a system;
(d) preventing or decreasing replication of a target RNA in a system;
(e) detecting the presence of a target RNA in a system;
(f) validating a gene target in a system;
(g) preventing or treating a disease related to a target RNA in a system; and
(h) any combination of (a) to (g).

The invention further provides a commercial package comprising the above-mentioned oligonucleotide together with instructions for its use. In an embodiment the instructions are for a use selected from the group consisting of:
(a) inducing RNase H-mediated cleavage of a target RNA in a system;
(b) preventing or decreasing translation of a target RNA in a system;
(c) preventing or decreasing reverse transcription of a target RNA in a system;
(d) preventing or decreasing replication of a target RNA in a system;
(e) detecting the presence of a target RNA in a system;
(f) validating a gene target in a system;
(g) preventing or treating a disease related to a target RNA in a system; and
(h) any combination of (a) to (g).

DETAILED DESCRIPTION OF THE INVENTION

Figure 1:
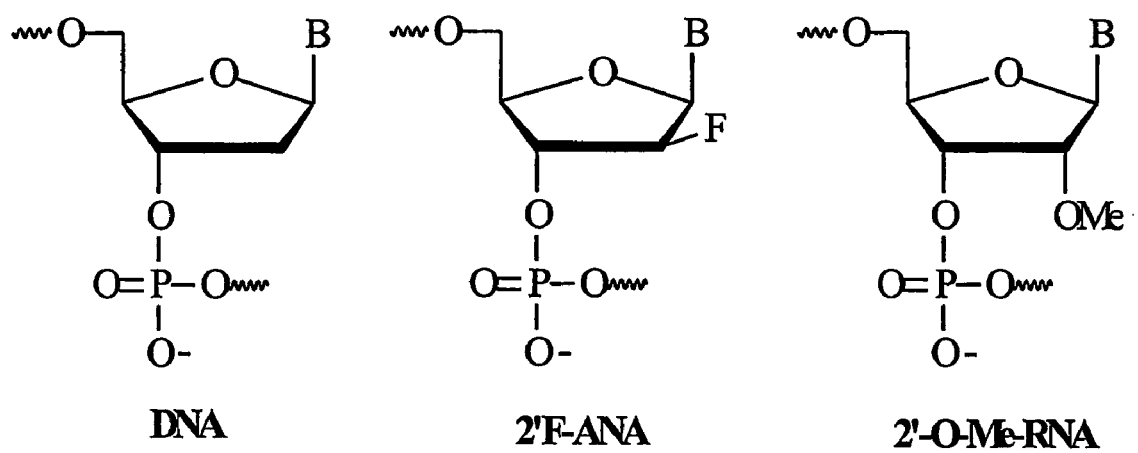
FIG. 1. Structures of examples of certain nucleotide components utilized in antisense oligonucleotides (AONs).

The invention relates to oligonucleosides comprising alternating segments ("altimers") of sugar-modified nucleosides and 2'-deoxynucleosides. In an embodiment, The oligonucleoside or nucleosides comprise a phosphate, thereby being oligonucleotide or nucleotides, respectively.

In an embodiment, such "altimers" comprise alternating segments of arabinonucleotide (ANA) such as 2'F-ANA (or FANA) and DNA. "Arabinonucleotide" as used herein refers to a nucleotide comprising an arabinofuranose sugar.

Results presented herein include studies of (1) oligonucleotide binding affinity to target RNA and (2) the ability of oligonucleotide to elicit RNase H cleavage of a target RNA. Both phosphodiester and phosphorothioate linked "altimers" were evaluated in the results described herein.

Accordingly, the invention relates to modified oligonucleotides which in embodiments are used to selectively prevent gene expression in a sequence-specific manner. In an embodiment, the invention relates to the selective inhibition of protein biosynthesis via an antisense strategy using short strands comprising alternating segments or units of sugar-modified nucleic acids (e.g. arabinonucleic acids [e.g. FANA]) and DNA. Each segment or unit may contain one or more nucleotides. In embodiments the invention relates to the use of modified oligonucleotides comprising alternating units of sugar-modified nucleic acids and DNA, to hybridize to complementary (in an embodiment, exactly complementary) RNA such as cellular messenger RNA, viral RNA, etc. In a further embodiment, the invention relates to the use of such modified oligonucleotides to hybridize to and induce cleavage of complementary RNA via RNase H activation/induction of RNase H activity.

In an embodiment, the invention relates to antisense oligonucleotide (AON) chimeras constructed from sugar-modified nucleotides and 2'-deoxyribonucleotides, which in certain embodiments are modified, that are capable of forming a duplex with a target RNA sequence. In an embodiment, the resulting AON/RNA duplexes are substrates for RNase H, an enzyme that recognizes such a duplex and degrades the RNA target portion. RNase H-mediated cleavage of RNA targets is considered to be a major mechanism of action of antisense oligonucleotides.

The present invention relates to the unexpected and surprising discovery that antisense chimeras constructed from alternating units or segments of a sugar-modified nucleotides such as modified ANA (such as 2'-deoxy-2'-fluoro-β-D-arabinonucleotides [FANA]), and 2'-deoxynucleotides (DNA), each unit containing one or more such residues, are superior at eliciting RNase H (e.g. eukaryotic RNase H) activity in vitro compared to (a) the native DNA structure, and (b) uniformly modified FANA oligomers. Similarly, the present invention shows that the RNase H competency of oligodeoxynucleotides (such as DNA) can be improved by inserting such sugar-modified nucleotides (e.g. arabinonucleotide [e.g. FANA]) residues within the oligonucleotide chain. Accordingly, oligonucleotides of the invention comprising alternating units or segments of (modified) sugar-modified nucleotide and deoxyribonucleotide, are useful as therapeutic agents and/or tools for the study and control of specific gene expression in cells and organisms, e.g. for a variety of medical and research uses. The oligonucleotides of the invention are also useful for diagnostic and detection methods to identify the presence of a particular nucleic acid, based on their ability to target the nucleic acid.

"Sugar-modified nucleoside" or "sugar-modified nucleotide" as used herein refers to a nucleoside or nucleotide, respectively, which has a different or modified sugar structure as compared to the sugar moiety of a native deoxyribonucleoside or deoxyribonucleotide, respectively, or ribonucleoside or ribonucleotide, respectively. Such modifications include but are not limited to changes in conformation of the sugar ring, substitution or addition of different ring structures, and the modification (substitution, deletion or addition) of any sugar ring substituents. In a further embodiment, such a sugar-modified nucleoside or nucleotide is capable of adopting a DNA-like conformation. A "DNA-like conformation" as used herein refers to the sugar structure of the nucleoside or nucleotide, and refers to a conformation which resembles the conformation of a native 2'-deoxyribonucleoside or 2'-deoxyribonucleotide residue, i.e. one whose sugar residue is capable of adopting a C2'-endo (south pucker) and/or O4'-endo (east pucker) conformation. As arabinonucleotides may adopt such a C2'-endo (south pucker) and/or O4'-endo (east pucker) conformation, arabinonucleic acids and DNA exhibit similar conformational preferences (Venkateswarlu, D. et al. J. Am. Chem. Soc. 1999, 121, 5609; Trempe, J-F. et al., J. Am. Chem. Soc. 2001, 123, 4896; Denisov, A. Y. et al., Nucleic Acids Res. 2001, 29, 4284), and thus in embodiments ANA and its derivatives (e.g. FANA), are a type of DNA-like nucleotide as defined herein. Other DNA-like nucleotides include but are not limited to alpha-L-LNA (Petersen, M. et al., J. Am. Chem. Soc. 2001; 123; 7431) and cyclohexene nucleic acids Wang, J. et al., J. Am. Chem. Soc., 2000, 122, 8595).

In embodiments, the internucleotide linkages of the oligonucleotides of the invention include but are not limited to phosphodiester, phosphotriester, phosphorothioate (5'O—P(S)O-3'O—, 5'S—P(O)O-3'O—, and 5'O—P(O)O-3'S—), phosphorodithioate, Rp-phosphorothioate, Sp-phosphorothioate, boranophosphate, methylene(methylimino), amide (3'-CH2-CO—NH-5' and 3'-CH2-NH—CO-5'), methylphosphonate, 3'-thioformacetal, (3'S—CH2-O5'), amide (3'CH2-C(O)NH-5'); phosphoramidate (e.g. 5'N-3'P) groups or any combinations thereof. The 2'-substituent, e.g. of the arabinose sugar in ANA residues, includes but is not limited to fluorine, hydroxyl, amino, cyano, azido, —CH=CH2, —C≡CH, alkyl (e.g. lower alkyl [e.g. C1-C9 alkyl] e.g. methyl, ethyl, propyl, etc.), alkoxy ([e.g. lower alkoxy, e.g. C1-C9 alkoxy] e.g. methoxy, ethoxy, proproxy, etc.) and functionalized alkyl (e.g. functionalized lower alkyl [e.g.2'-CF3]) and alkoxy groups (e.g. ethylamino, propylamino and butylamino groups), and alkoxyalkyl (e.g. methoxyethyl, ethoxyethyl, etc.) groups. In an embodiment, the 2' substituent of the arabinose sugar is fluorine and the arabinonucleotide derivative is 2'F-ANA (or FANA). In addition to those described above, the arabinose sugar also includes the carbocyclic (4'-CH2) derivative (e.g., carbocyclic FANA). In embodiments, the sugar modified nucleotide comprises other backbones that elicit RNase H activity (e.g., alpha-L-locked nucleic acids, cyclohexene nucleic acids), or by riboses lacking the electronegative 2'-oxygen atom (e.g., 2'-alkyl-D-ribose, 2'-SCH3-D-ribose).

Applicants demonstrate herein that mixed backbone AON comprising alternating segments of a sugar-modified nucleotide (e.g. ANA [e.g. FANA]) and DNA ("altimers") are capable of eliciting RNase H (e.g. human RNase HII) degradation of target RNA. Certain "altimer" AON, namely those possessing alternating trinucleotide segments, are particularly better in this regard.

Therefore, an oligonucleotide of the invention comprises alternating segments or units of sugar-modified nucleotides (e.g. arabinonucleotide analogues [e.g., FANA]) and 2'-deoxyribonucleotides (DNA). In an embodiment, the oligonucleotide comprises at least 2 of each of sugar-modified nucleotide and 2'-deoxynucleotide segments, thereby having at least 4 alternating segments overall. Each alternating segment or unit may contain 1 or a plurality of nucleotides. In embodiments, the plurality of nucleotides may consist of 2, 3, 4, 5 or 6 nucleotides. The oligonucleotide may contain in embodiments an odd or even number of alternating segments or units. The oligonucleotide may commence and/or terminate with a segment containing sugar-modified nucleotide residues or DNA residues. Accordingly, in embodiments, the oligonucleotides of the invention may be represented as follows:

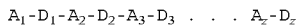

Where each of $A_1$, $A_2$, etc. represents a unit of one or more sugar-modified nucleotide residues and each of $D_1$, $D_2$, etc. represents a unit of one or more DNA residues. The number of residues within each unit may be the same or variable from one unit to another. The oligonucleotide may have an odd or an even number of units. The oligonucleotide may start (i.e. at its 5' end) with either an ANA-containing unit or a DNA-containing unit. The oligonucleotide may terminate (i.e. at its 3' end) with either an sugar-modified nucleotide-containing unit or a DNA-containing unit. The total number of units may be as few as 4 (i.e. at least 2 of each type).

In embodiments, the "altimer" portion of an oligonucleoside or oligonucleotide of the invention may further comprise one or more modified nucleosides or nucleotides at (i.e. adjacent to) its 5' and/or 3' ends, including but not limited to modified ribonucleosides or ribonucleotides, such as 2'-modified ribonucleosides or ribonucleotides, such as 2'-methoxy RNA (2'-O-Me-RNA) or 2'-methoxyethyl RNA (2'-MOE-RNA). Such a 2'-O-Me-RNA-altimer-2'-Ome-RNA based oligonucleotide is capable of eliciting RNase H activity of a suitable RNA target, as described in the Examples herein.

In embodiments, the overall length of an oligonucleotide of the invention is about 30 or fewer nucleotide residues, in a further embodiment about 8 to about 25 nucleotide residues. In further embodiments, the length is about 9 to about 24, about 10 to about 23, about 11 to about 22, about 12 to about 21, about 13 to about 20, about 14 to about 19, about 15 to about 18, or about 16 to about 17 nucleotide residues. In an embodiment, the length of an oligonucleotide of the invention is 18 nucleotide residues.

In embodiments, DNA residues may contain any of the bases selected amongst adenine (A), cytosine (C), guanine (G) or thymine (T) or versions comprising modifications of the nucleotide base or backbone structures. In embodiments, ANA residues may contain any of the bases selected amongst adenine (A), inosine (I), 2,6-diaminopurine (2,6-DAP), cytosine (C), 5-methylcytosine (5 meC), guanine (G) or thymine (T) or uracil (U).

The AONs of this invention contain a sequence that is complementary (in certain embodiments partially complementary, and in other embodiments exactly complementary) to a "target RNA". "Hybridization" as used herein refers to hydrogen bonding between complementary nucleotides. The degree of complementarity between an AON and its target sequence may be variable, and in embodiments the AON is exactly complementary to its target sequence as noted above. It is understood that it is not essential that an AON be exactly complementary to its target sequence to achieve sufficient specificity, i.e. to minimize non-specific binding of the oligonucleotide to non-target sequences under the particular binding conditions being used (e.g. in vivo physiological conditions or in vitro assay conditions). "Target RNA" refers to an RNA molecule of interest which is the target for hybridizing with/binding to an oligonucleotide of the invention to prevent or decrease for example the translation, reverse transcription and or replication of the RNA. In embodiments, such prevention and inhibition is via an induction of RNase H-mediated cleavage of the target RNA, and therefore in an embodiment, the invention provides a method of cleaving a target RNA, said method comprising contacting the RNA with an oligonucleotide of the invention. In embodiments, such cleavage may be further facilitated by additionally providing conditions conducive to RNase H activity, such as buffer means (e.g. to control pH and ionic strength), temperature control means, and any other components which may contribute to an induction in RNase H activity. In certain embodiments, RNase H activity is of an RNase H enzyme or of a multifunctional enzyme possessing RNase H activity (e.g., HIV reverse transcriptase). In certain embodiments, such RNase H activity includes, but is not limited to RNase H activity associated with the reverse transcriptases of human pathogenic viruses such as HIV (e.g. the retroviruses HIV-1 and HIV-2) and hepadnavirus, e.g. hepatitis B virus. In further embodiments, such RNase H activity includes, but is not limited to RNase H activity associated with an RNase H enzyme of prokaryotic or eukaryotic origin, in an embodiment, of mammalian origin, in an embodiment, of human origin. In further embodiments, such RNase H activity includes, but is not limited to RNase H activity associated with RNase H1 and RNase H2 (sometimes referred to as RNase HII) of eukaryotic or prokaryotic origin. In an embodiment, such RNase H activity is associated with human RNase H2.

In embodiments, the above-noted RNA includes messenger RNA, or viral genomic RNA, such that the oligonucleotide can specifically inhibit the biosynthesis of proteins encoded by the mRNA, or inhibit virus replication, respectively. Partial modifications to the oligonucleotide directed to the 5' and/or 3'-terminus, or the phosphate backbone or sugar residues to enhance their antisense properties (e.g. nuclease resistance) are within the scope of the invention. As demonstrated in this invention (vida infra), these oligonucleotides meet one of the requirements for antisense therapeutics, i.e., they are capable of binding to target RNA forming an AON/RNA duplex, which in an embodiment is recognized and degraded by RNase H. Furthermore, as shown in the Examples below, the efficiency by which the "altimer" oligonucleotides of the invention promote RNA cleavage is superior to that seen with AON containing only FANA and in some cases superior that seen with AON containing only DNA residues. This holds true whether the internucleotide linkages of the "altimer" are phosphodiester or phosphorothioate linkages.

Therefore, the results presented herein establish that the "altimer"-comprising oligonucleosides or oligonucleotides of the invention can in embodiments be used as antisense agents, and should serve as therapeutics and/or valuable tools for studying and controlling gene expression in cells and organisms.

As such, in alternative embodiments, the invention provides antisense molecules that bind to, induce degradation of and/or inhibit the translation of (e.g. by inducing RNase H activity and/or by effecting "translational arrest" or blocking) a target RNA (e.g. mRNA). Examples of therapeutic antisense oligonucleotide applications, incorporated herein by reference, include: U.S. Pat. No. 5,135,917, issued Aug. 4, 1992; U.S. Pat. No. 5,098,890, issued Mar. 24, 1992; U.S. Pat. No. 5,087,617, issued Feb. 11, 1992; U.S. Pat. No. 5,166,195 issued Nov. 24, 1992; U.S. Pat. No. 5,004,810, issued Apr. 2, 1991; U.S. Pat. No. 5,194,428, issued Mar. 16, 1993; U.S. Pat. No. 4,806,463, issued Feb. 21, 1989; U.S. Pat. No. 5,286,717 issued Feb. 15, 1994; U.S. Pat. No. 5,276,019 and U.S. Pat. No. 5,264,423; BioWorld Today, Apr. 29, 1994, p. 3.

Preferably, in antisense molecules, there is a sufficient degree of complementarity to the target RNA to avoid non-specific binding of the antisense molecule to non-target sequences under conditions in which specific binding is desired, such as under physiological conditions in the case of in vivo assays or therapeutic treatment or, in the case of in vitro assays, under conditions in which the assays are conducted. The target RNA for antisense binding may include not only the information to encode a protein, but also associated ribonucleotides, which for example form the 5'-untranslated region, the 3'-untranslated region, the 5' cap region and intron/exon junction ribonucleotides. A method of screening for antisense and ribozyme nucleic acids that may be used to provide such molecules as $PLA_2$ inhibitors of the invention is disclosed in U.S. Pat. No. 5,932,435.

Antisense molecules (oligonucleosides or oligonucleotides) of the invention may include those which contain intersugar backbone linkages such as phosphotriesters, methyl phosphonates, 3'-thioformacetal, amide, short chain alkyl or cycloalkyl intersugar linkages or short chain heteroatomic or heterocyclic intersugar linkages, phosphorothioates and those with $CH_2$—NH—O—$CH_2$, $CH_2$—N($CH_3$)—O—$CH_2$ (known as methylene(methylimino) or MMI backbone), $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P(O)$_2$—O—$CH_2$). In alternative embodiments, antisense oligonucleotides may have a peptide nucleic acid (PNA, sometimes referred to as "protein" or "peptide" nucleic acid) backbone, in which the phosphodiester backbone of the oligonucleotide may be replaced with a polyamide backbone wherein nucleosidic bases are bound directly or indirectly to aza nitrogen atoms or methylene groups in the polyamide backbone (Nielsen et al., Science, 1991, 254, 1497 and U.S. Pat. No. 5,539,082). The phosphodiester bonds may be substituted with structures that are chiral and enantiomerically specific.

As noted above, oligonucleotides may also include species which include at least one modified nucleotide base. Thus, purines and pyrimidines other than those normally found in nature may be used. As noted above, a nucleotide of the sugar-modified nucleotide segment (e.g. ANA segment) may comprise modifications on its pentofuranosyl portion. Examples of such modifications are 2'-O—alkyl- and 2'-halogen-substituted nucleotides. Some specific examples of modifications at the 2' position of sugar moieties which are useful in the present invention are OH, SH, $SCH_3$, F, OCN, $O(CH_2)_n NH_2$ or $O(CH_2)_n CH_3$ where n is from 1 to about 10; $C_1$ to $C_{10}$ lower alkyl, substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2 CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. One or more pentofuranosyl groups of the nucleotide of the sugar-modified nucleotide segment may be replaced by another sugar, by a sugar mimic such as cyclobutyl or by another moiety which takes the place of the sugar.

"Nucleoside" refers to a base (e.g. a purine [e.g. A and G] or pyrimidine [e.g. C, 5-methyl-C, T and U]) combined with a sugar (e.g. [deoxy]ribose, arabinose and derivatives). "Nucleotide" refers to a nucleoside having a phosphate group attached to its sugar moiety. In embodiments these structures may include various modifications, e.g. either in the base, sugar and/or phosphate moieties. "Modified nucleotide/nucleoside" as used herein refers to a nucleotide/nucleoside that differs from and thus excludes the defined native form.

"Oligonucleotide" as used herein refers to a sequence comprising a plurality of nucleotides joined together. An oligonucleotide may comprise modified structures in its backbone structure and/or in one or more of its component nucleotides. In embodiments, oligonucleotides of the invention are about 1 to 200 bases in length, in further embodiments from about 5 to about 50 bases, from about 8 to about 40 bases, and yet further embodiments, from about 12 to about 25 bases in length.

"Alkyl" refers to straight and branched chain saturated hydrocarbon groups (e.g. methyl, ethyl, propyl, butyl, isopropyl etc.). "Alkenyl" and "alkynyl" refer to hydrocarbon groups having at least one C—C double and one C—C triple bond, respectively. "Alkoxy" refers to an —O-alkyl structure. "Alkylamino" refers to —NH(alkyl) or —N(alkyl)$_2$ structures. "Aryl" refers to substituted and unsubstituted aromatic cyclic structures (e.g. phenyl, naphthyl, anthracyl, phenanthryl, pyrenyl, and xylyl groups). "Hetero" refers to an atom other than C; including but not limited to N, O, or S. In embodiments, the above-mentioned groups may be substituted.

Accordingly, in various embodiments, a modified oligonucleotide of the invention may be used therapeutically in formulations or medicaments to prevent or treat a disease characterized by the expression of a particular target RNA. In certain embodiments, such a target nucleic acid is contained in or derived from an infectious agent and/or is required for the function and/or viability and/or replication/propagation of the infectious agent. In certain embodiments, such an infectious agent is a virus, in certain embodiments, a retrovirus, in a further embodiment, HIV. In further embodiments the expression of such a target nucleic acid is associated with the diseases including but not limited to inflammatory diseases, diabetes, cardiovascular disease (e.g. restinosis), and cancer. The invention provides corresponding methods of medical treatment, in which a therapeutic dose of a modified oligonucleotide of the invention is administered in a pharmacologically acceptable formulation. Accordingly, the invention also provides therapeutic compositions comprising a modified oligonucleotide of the invention, and a pharmacologically acceptable excipient or carrier. The therapeutic composition may be soluble in an aqueous solution at a physiologically acceptable pH.

In an embodiment, such compositions include an oligonucleotide of the invention in a therapeutically or prophylactically effective amount sufficient to treat or prevent a disease characterized by the expression of a particular target nucleic acid, and a pharmaceutically acceptable carrier.

A "therapeutically effective amount" refers to an amount effective, at dosages and for periods of time necessary, to achieve the desired therapeutic result, such as a decrease in or a prevention of the expression of a particular target nucleic acid. A therapeutically effective amount of a modified nucleic acid of the invention may vary according to factors such as the disease state, age, sex, and weight of the individual, and the ability of the modified nucleic acid to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as preventing or treating a disease characterized by the expression of a particular target nucleic acid. A prophylactically effective amount can be determined as described above for the therapeutically effective amount. For any particular subject, specific dosage regimens may be adjusted over time according to the individual need and the professional judgement of the person administering or supervising the administration of the compositions.

As used herein "pharmaceutically acceptable carrier" or "excipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, an oligonucleotide of the invention can be administered in a time release formulation, for example in a composition which includes a slow release polymer. The modified oligonucleotide can be prepared with carriers that will protect the modified oligonucleotide against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating an active compound, such as an oligonucleotide of the invention, in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In accordance with an alternative aspect of the invention, an oligonucleotide of the invention may be formulated with one or more additional compounds that enhance its solubility.

Since the oligonucleotides of the invention are capable of inducing the RNase H-mediated cleavage of a target RNA, thus decreasing the production of the protein encoded by the target RNA, the modified oligonucleotides of the invention may be used in any system where the selective inactivation or inhibition of a particular target RNA is desirable. As noted above, examples of such uses include antisense therapeutics, in which expression of the target RNA is associated with illness or disease.

A further example of such a use is the selective depletion of a particular target gene product in a system to study the phenotypic effect(s) of such depletion on the system. Observations made via such depletion studies may thus allow the determination of the function of the target gene product. In certain embodiments, such uses include "target validation", in which the above-described strategy enables the confirmation as to whether a particular target nucleic acid is associated with a particular phenotype or activity, and thus allows "validation" of the target. The above noted system may be cell or cell-free; in vitro or in vivo; prokaryotic or eukaryotic.

The invention further provides commercial packages comprising an oligonucleotide of the invention. In an embodiment, the commercial package further comprises instructions for use of the oligonucleotide. In certain embodiments, such instructions for use include at least one of the following: use of the oligonucleotide for (a) decreasing the expression of a target RNA sequence; (b) inducing the RNase H cleavage of a target RNA sequence; (c) preventing or treating a disease characterized by the expression of a particular RNA target; (d) preventing or decreasing reverse transcription of a target RNA in a system; (e) preventing or decreasing replication of a target RNA in a system; (f) detecting the presence of a target RNA in a system; (g) validating a gene target in a system; and (h) any combination of (a) to (g).

The invention further provides a use of an oligonucleotide of the invention, such as for (a) decreasing the expression of a target RNA sequence; (b) inducing the RNase H cleavage of a target, RNA sequence; (c) preventing or treating a disease characterized by the expression of a particular RNA target; (d) preventing or decreasing reverse transcription of a target RNA in a system; (e) preventing or decreasing replication of a target RNA in a system; (f) detecting the presence of a target RNA in a system; (g) validating a gene target in a system; and (h) any combination of (a) to (g).

The invention further provides a use of an oligonucleotide of the invention for the preparation of a medicament, such as for (a) decreasing the expression of a target RNA sequence; (b) inducing the RNase H cleavage of a target RNA sequence; (c) preventing or treating a disease characterized by the expression of a particular RNA target; (d) preventing or decreasing reverse transcription of a target RNA in a system; (e) preventing or decreasing replication of a target RNA in a system; (f) detecting the presence of a target RNA in a system; (g) validating a gene target in a system; and (h) any combination of (a) to (g).

Although various embodiments of the invention are disclosed herein, many adaptations and modifications may be made within the scope of the invention in accordance with the common general knowledge of those skilled in this art. Such, modifications include the substitution of known equivalents for any aspect of the invention in order to achieve the same result in substantially the same way. Numeric ranges are inclusive of the numbers defining the range. In the claims, the word "comprising" is used as an open-ended term, substantially equivalent to the phrase "including, but not limited to". The following examples are illustrative of various aspects of the invention, and do not limit the broad aspects of the invention as disclosed herein.

EXAMPLES

Example 1

Materials and Methods

Synthesis of AONs. 5'-Monomethoxytritylated 2'-deoxy-2'-fluoroarabinonucleoside 3'-O-cyanoethylphosphoramidite monomers were synthesized as previously described [Wilds, C. J. & Damha, M. J. *Nucleic Acids Res.* 2000, 28, 3625; Elzagheid, M. I. et al., In *Current Protocols in Nucleic Acid Chemistry*, Unit 1.7, Beaucage, S. L., Bergstrom, D. E., Gli, G. D., Eds., 2002]. Synthesis of oligonucleotides shown on Table 1 and 2 were synthesized on a 1-micromole scale using an Expedite 8909 DNA-synthesizer. Long-chain alkylamine controlled-pore glass (LCAA-CPG) was used as the solid support. The synthesis cycle consisted of the following steps: (a) Detritylation of nucleoside/tide bound to CPG (3% trichloroacetic acid/dichloromethane): 150 sec.; (b) coupling of 2'-F-arabinonucleoside (15 min) or 2'-deoxyribonucleoside 3'-phosphoramidite (2 min) monomers. Concentration of monomers used were 50 mg/mL for araF-T, araF-C and DNA monomers, and 60 mg/mL for araA and araF-G (acetonitrile as solvent); (c) acetylation using the standard capping step: 20 sec. The capping solution consisted of 1:1 (v/v) of "cap A" and "cap B" reagents. (Cap A: acetic anhydride/collidine/THF, 1:1:8; cap B: N-Methylimidazole/THF, 4:21); (d) extensive washing with acetonitrile (50 pulses); (e) 20-second iodine/water oxidation (in the case of phosphodiester linked oligomers) or 10-min sulfuration (in the case of PS-oligomers) with a fresh solution of 0.1 M 3-amino-1,2,4-dithiazoline-5-thione (ADTT) in pyridine/acetonitrile (1/1, v/v); (f) washing with acetonitrile: 20 pulses; (g) drying of the solid support by addition of the capping reagent (see step c above): 5 sec; (h) washing with acetonitrile (20 pulses). Following chain assembly, oligonucleotides were cleaved from the solid support and deprotected as previously described [Wilds, C. J. & Damha, M. J. *Nucleic Acids Res.* 2000, 28, 3625; Viazovkina, E. et al., In *Current Protocols in Nucleic Acid Chemistry*, Unit 4.15, Beaucage, S. L., Bergstrom, D. E., Gli, G. D., Eds., 2002]. The crude oligomers were purified by anion-exchange HPLC followed by desalting (SepPak cartridges). Yields: 50-100 $A_{260}$ units. Conditions for HPLC Purification: Column: Protein Pak DEAE-5PW (7.5 mm×7.5 cm, Waters), Solvents: Buffer A: $H_2O$; Buffer B: 1M $LiClO_4$ (or 1M $NaClO_4$), Gradient: 100% buffer A isocratic for 12 min, 100% A-15% B, linear (over 5 min), 15% B-55% B, linear (over 60 min); Flow rate was set at 1 ml/min, temperature was adjusted to 50° C. The detector was set at 260 nm for analytical and 290 nm for preparative chromatography. Under these conditions, the desired full-length oligomer eluted last. Oligonucleotides were characterized by gel electrophoresis and mass spectrometry. Sequences of the oligonucleotides used are provided in Tables 1 and 2.

$T_m$ measurements. AON and complementary target RNA oligonucleotides were mixed in equimolar ratios in 140 mM KCl, 1 mM $MgCl_2$, and 5 mM $Na_2HPO_4$ buffer, pH 7.2, to provide a total duplex concentration of ca. 5 µM. Samples were heated to 90° C. for 15 min, then cooled slowly to room temperature. The AON/RNA duplex solution was then exposed to increasing temperature (0.5° C./measurement), and the UV absorbance at 260 nm was determined after temperature equilibration. $T_m$ values provided on Table 1 and 2 were calculated using the base-line method and have an uncertainty of ±0.5° C.

Purification of RNase H. *E. coli* RNase HI was purified as described previously (7). Human RNase HII was over-expressed and purified following published procedures (Wu, H. et al., *J. Biol. Chem.*, 1999, 274, 28270).

RNase H assay. RNase H assays were carried out at room temperature (≈20° C.) (homopolymeric oligonucleotides shown in Table 1), or 37° C. (mixed-based oligonucleotides shown in Table 2). Homopolymeric nucleic acid duplex substrates were prepared by mixing the phosphodiester linked AON (2 pmol) with 5'-$^{32}$P-labeled complementary target oligo-$rA_{18}$ RNA (0.5 pmol; SEQ ID NO: 21) in 10 µl of 60 mM Tris-HCl (pH 7.8) containing 60 mM KCl and 2.5 mM $MgCl_2$, followed by heating at 90° C. for 2 minutes and slow cooling to room temperature. Duplex substrate solutions were allowed to stand at room temperature for at least 1 h prior to use. Reactions were initiated by the addition of RNase H (7 ng of enzyme in 2 µL buffer) and aliquots were removed at various times and quenched by the addition of an equal volume of 98% deionized formamide containing 10 mM EDTA, 1 mg/mL bromophenol blue and 1 mg/mL xylene cyanol. After heating at 100° C. for 5 min, reaction products were resolved by electrophoresis on 16% polyacrylamide sequencing gels containing 7 M urea, visualized by autoradiography, and product formation was quantified by densitometry.

AON/RNA hybrids of mixed base composition were prepared by mixing the phosphorothioate AON strand (see oligomers listed on Table 2) with the corresponding 5'-radiolabeled target RNA (AAG GGA UAC GAC AAG GAU AUA A [SEQ ID NO: 22]). This RNA was 5'-end labeled with 32P using [γ-$^{32}$P]-ATP using T4 polynucleotide kinase. Twenty pmol (20 pmol) antisense oligonucleotides and 10 pmol 5'-32P-labeled RNA were mixed in a buffer (100 µl final) containing 60 mM Tris.HCl (pH 7.8), 60 mM KCl, 2.5 mM $MgCl_2$, heated at 90° C. for 5 minutes and slowly cooled to room temperature. To initiate reactions, human RNase H (5 ng in 2 µl buffer) was added to 8 µl of the above substrate solution. After incubation at 37° C., the reactions were terminated by adding an equal volume of denaturing loading buffer (98% deionized formamide, 10 mM EDTA, 1 mg/mL bromophenol blue and 1 mg/mL xylene cyanol). The products were separated on a denaturing 16% gel (w/v) polyacrylamide/7 M urea gel in Tris-borate/EDTA buffer at 2000 V for approximately 2 h. After electrophoresis, the gel was exposed to an X-ray film and the resulting autoradiograms were scanned and quantitated.

Luciferase assay. HeLa X1/5 cells (stably transfected with the luciferase gene and expressing a functional luciferase enzyme) were cultured in Dulbecco's modified Eagle's medium (DMEM) supplemented with 10% fetal bovine serum (FBS). Cells were seeded in 96-well plates at 2×104 cells/well. Antisense experiments were carried out 24 h after seeding, by which time cells were 80% confluent. Lipofectin was used to deliver antisense oligonucleotides to the cells. Briefly, antisense oligonucleotides and Lipofectin were diluted with DMEM without serum to provide a 10× final concentration of antisense and 50 µg/ml Lipofectin. Equal volumes of oligonucleotide and Lipofectin solutions were mixed in plastic tubes and incubated for 15 min at room temperature to allow complex formation. This complex was diluted 5-fold with DMEM containing 10% FBS, and then the cell culture medium was replaced with this mixture and cells incubated for 4 hours at 37° C. The antisense/Lipofectin mixture was removed from the cells and replaced with DMEM containing 10% FBS, and then the cells were incubated for an additional 16 hours at 37° C. After this additional 16 hours incubation, cellular luciferase activity was assessed using the luciferase assay system (Promega, Madison, Wis., USA) according to the manufacturer's protocol. Briefly, the culture medium was removed, the cells were washed with phosphate-buffered saline, and then the cells were lysed. Aliquots of the cell lysates were transferred to assay microplates, luciferin substrate solution was added, and the resulting luminescence was immediately measured using a SPECTRAmax GEMINI XS microplate spectrofluorometer (Molecular Devices, Sunnyvale, Calif., USA) set at luminescence reading mode.

Example 2

Stability of Altimer:RNA Duplexes

Applicants demonstrate herein that ANA/DNA (e.g. FANA/DNA) "altimer" oligonucleotides form duplexes with target RNA (Tables 1 & 2), and that the melting temperature for these AON chimeras directly correlates with the FANA content. Previous studies have shown that 2'-OMe RNA AON also bind to target RNA with a higher affinity than do the corresponding DNA AON. However, mixed backbone 2'-OMe RNA/DNA AON (SEQ ID Nos: 8-10) showed only similar or lower thermal binding affinity for target RNA compared to the all DNA AON (SEQ ID NO: 1).

TABLE 1

Altimer AONs and their duplex formation with target octadecariboadenylic acid (r-$A_{18}$).

| AON NO. or SEQ ID NO: | AON Sequence[a] | Tm (° C.) |
|---|---|---|
| 1 | 5'-TTT TTT TTT TTT TTT TTT-3' | 40 |
| 2 | 5'-FFF FFF FFF FFF FFF FFF-3' | 53 |
| 3 | 5'-FTF TFT FTF TFT FTF TFT-3' | 45.5 |
| 4 | 5'-FFT TFF TTF FTT FFT TFF-3' | 46 |
| 5 | 5'-FFF TTT FFF TTT FFF TTT-3' | 47 |
| 6 | 5'-FFT FTT TFF FFT TTF FFF-3' | 47 |
| 7 | 5'-FFF FFF TTT TTT FFF FFF-3' | 48 |
| 8 | 5'-UTU TUT UTU TUT UTU TUT-3' | 33 |
| 9 | 5'-UUU TTT UUU TTT UUU TTT-3' | 42 |
| 10 | 5'-UUUUUU TTT TTT UUUUUU-3' | 41 |

[a]T, F, and U refer, respectively, to the natural 2'-deoxyribothymidine nucleotide, 2'-deoxy-2'-fluoro-D-arabinothymidine nucleotide, and 2'-O-methyl-D-uridine nucleotide. Tm is the melting temperature of the AON/RNA duplex, which is defined as the temperature at which half the population (50%) of molecules are duplexed (AON/RNA), and the remainder being single stranded (AON + RNA). Thus Tm values are an indication of the stability of the AON/RNA duplex.

Example 3

Ability of AON of the Invention to Elicit RNase H Degradation of Target RNA

Figure 2:
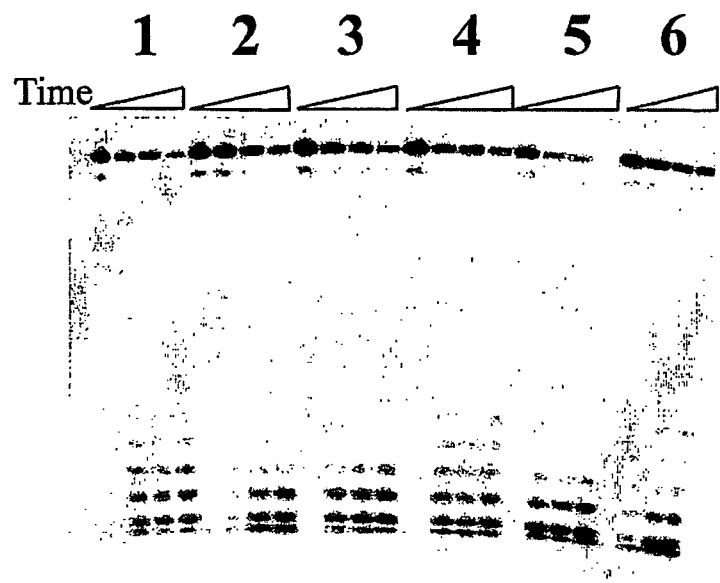
FIG. 2. Human RNase HII mediated cleavage of RNA duplexed with various antisense oligonucleotides according to certain embodiments of the invention. (A). Electrophoretic analysis of $^{32}$P-labeled target RNA degradation products. AON/5'-[$^{32}$P]-RNA duplexes were incubated with human RNase HII at room temperature, and aliquots were taken at 0, 5, 10, and 20 min, electrophoresed and reaction products visualized by autoradiography. (B). Residual full-length 5'-[$^{32}$P]-target as a function of reaction time. Data were obtained by densitometric analysis of the autoradiogram shown in A.
Figure 2:
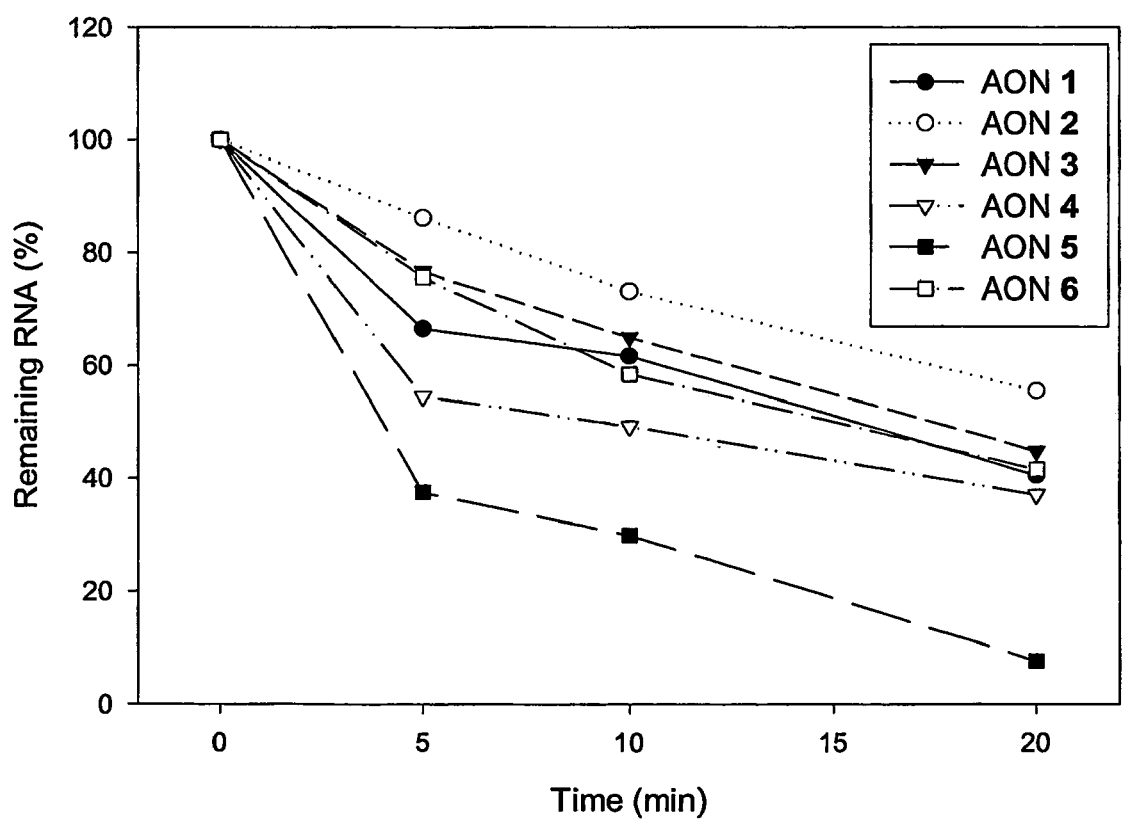

Studies with mixed backbone AON suggest that the ability of these AON to elicit RNase H degradation of the target RNA in vitro is predictive of the ability of these AON to inhibit intracellular gene expression (Monia, B. P. et al. *J. Biol. Chem.* 1993, 268, 14514; Gutierrez, A. J. et al., *Biochemistry* 1997, 36, 743; Flanagan, W. M. et al., *Proc. Natl. Acad. Sci. U.S.A* 1999, 96, 3513). Applicants therefore evaluated duplexes of the various AON listed in Table 1 bound to complementary RNA as substrates for *E. coli* RNase HI and human RNase HII. FIG. 2 shows that all FANA/DNA chimeras induced target RNA cleavage by human RNase HII. RNase H cleavage efficiency increased as the size of the alternating DNA segments within the FANA background was increased. Optimal activity was noted with SEQ ID NO: 5, which comprises alternating trinucleotide segments of FANA and DNA. The ability of this "altimer" AON to elicit human RNase HII degradation of target RNA was significantly better than that of the equivalent all-DNA SEQ ID NO: 1. Furthermore, this characteristic of SEQ ID NO: 5 was improved relative to the FANA/DNA/FANA SEQ ID NO: 7 (FIG. 3).

Figure 3:
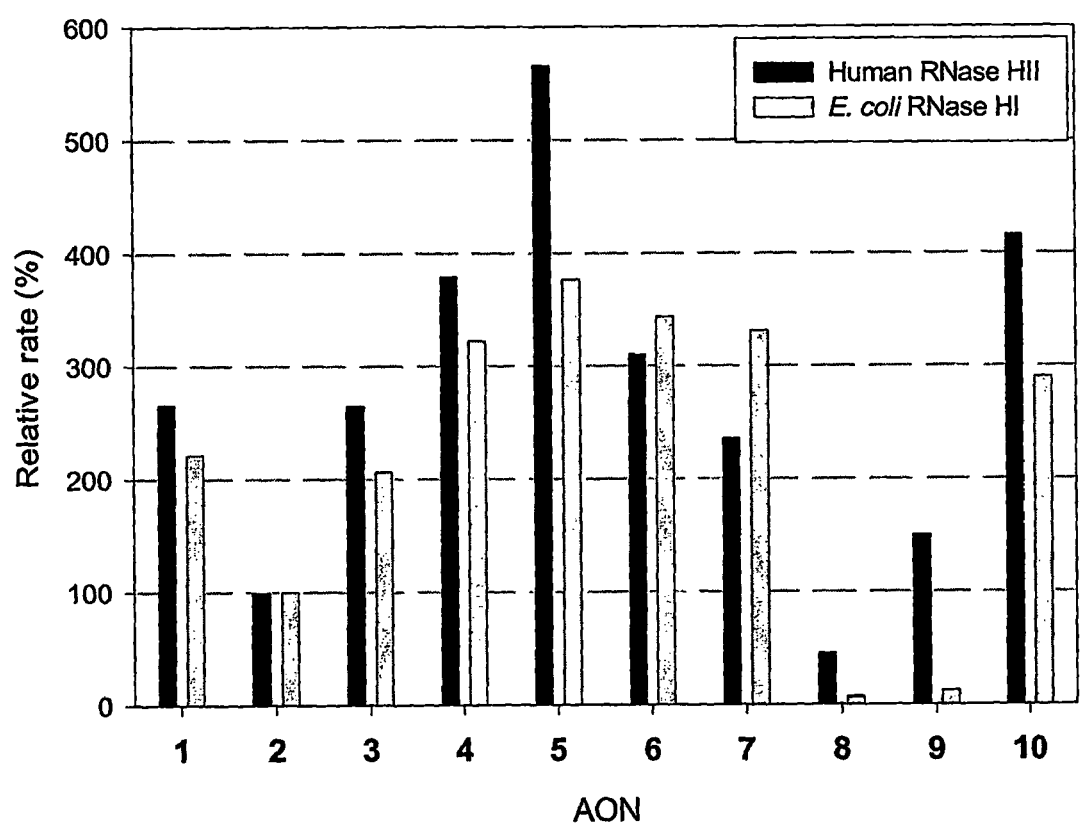
FIG. 3. Ability of the various AON listed in Table 1, according to certain embodiments of the invention, to elicit RNase H degradation of target RNA. AON/5'-[$^{32}$P]-RNA duplexes were incubated with human RNase HII (black bars) or *E. Coli* RNase HI (shaded bars) for 10 minutes at room temperature, then the reaction mixtures were resolved by electrophoresis, visualized by autoradiography, and the loss of intact RNA was quantified by densitometry. Values are normalized to those found for the all 2'F-ANA AON 2 as 100%.

Unlike "altimer" AON comprised of FANA and DNA, similar AON (SEQ ID NOs: 8 and 9) comprised of 2'-O-methyl RNA and DNA showed only poor ability to elicit RNase H degradation of target RNA (FIG. 3).

Example 4

Effect of Antisense Oligonucleotides on Luciferase Expression

Various oligonucleotides were prepared and characterized for binding to a luciferase-encoding target RNA, and assayed for their effect on luciferase expression, as described above. Results are presented in Table 2. With the exception of the "scrambled" and "mismatch" controls shown below, all oligonucleotides comprising FANA/DNA alternating segments exhibited significant inhibition of luciferase activity. While such inhibition was greatest with an oligonucleotide of 3-nucleotide alternating segments (SEQ ID NO: 12), it was also observed in the cases where flanking 2'-methoxy RNA nucleotides were added to a FANA/DNA alternating oligonucleotide (e.g. SEQ ID NOs: 15 and 16). Oligonucleotides comprising FANA/DNA alternating segments were superior in this regard as compared to a pure DNA oligonucleotide (SEQ ID NO: 11) or a 2'-methoxy RNA-DNA-2'-methoxy RNA "gapmer" oligonucleotide (SEQ ID NO: 20) which only exhibited very marginal levels of inhibition as compared to non-oligonucleotide controls.

TABLE 2

Table 2: Physical and Biological Properties of AON Oligonucleotides

| SEQ ID NO: | AON Sequence[a] | Tm ° C. | $k_{rel}$[b] | Luciferase Activity[c] (%) |
|---|---|---|---|---|
| 11 | Ata-tcc-ttg-tcg-tat-ccc | 57 | 3.4 | 80 |
| 12 | ATA-tcc-TTG-tcg-TAT-ccc | 62 | 4.2 | 21 |
| 13 | ATATCCTT-gtcgtatccc | 61 | 2.9 | 60 |
| 14 | TA gct CCA ca CTA ga CC (scrambled altimer control) | n.a. | n.d. | 102 |
| 15 | [2'OMe-AUAU]-cc-TT-gt-CG-ta [2'OMe-UCCC] | 66 | 3.3 | 57 |
| 16 | [2'OMe-AUAU]-CCT-tgt-CG-ta- [2'OMe-UCCC] | 66 | 3.3 | 42 |
| 17 | [2'OMe-AUAU]-CCTTG-tcgta- [2'Ome-UCCC] | 65 | 3.8 | 76 |

TABLE 2-continued

Table 2: Physical and Biological Properties of AON Oligonucleotides

| SEQ ID NO: | AON Sequence[a] | Tm °C. | $k_{rel}$[b] | Luciferase Activity[c] (%) |
|---|---|---|---|---|
| 18 | [2'OMe-AUAU]-CCTTGTCGTA-[2'OMe-UCCC] | 68 | 0.3 | 53 |
| 19 | [2'OMe-AUAA]-cct-tTt-cTt-A-[2'OMe-ACCC] (4 bp mismatch control) | n.a. | n.d. | 98 |
| 20 | [2'OMe-AUAU]-ccttgtcgta-[2'OMe-UCCC] | 64 | 3.6 | 82 |

[a]Lower case letters, DNA; Upper case bold letters, FANA; Upper case letters in square brackets, 2'-OMe-RNA. All AONs are phosphorothioates (all PS linkages).
[b]Pseudo-first rate constants for RNase-HII mediated hydrolysis of target RNA when duplexed to AON.
[c]The column "luciferase activity (%)" gives luciferase activity expressed as percent relative to luciferase activity in the absence of AON. Concentration of AON was 250 nM. N.a. = not applicable; n.d. = not determined.

The invention claimed is:

1. An oligonucleotide comprising alternating first and second segments, wherein:
   said first segment consists of all arabinonucleotides and comprises at least one arabinonucleotide
   said second segment consists of all 2'-deoxyribonucleotides and comprises at least one 2'-deoxyribonucleotide
   said oligonucleotide comprises at least 2 of each of said first and second segments thereby comprising at least 4 alternating segments wherein the number of residues within each first segments and each second segments may be the same or variable from one segment to another,
   at least one first segment comprises at least two arabinonucleotides and at least one second segment comprises at least two 2'-deoxyribonucleotides, and
   all internucleotide linkages of the oligonucleotide consist of phosphorothioate linkages.

2. The oligonucleotide of claim 1, wherein said oligonucleotide is capable of adopting a DNA-like conformation.

3. The oligonucleotide of claim 1, wherein all arabinonucleoides have flourine as A 2' substitute.

4. The oligonucleotide of claim 1, wherein said segments each independently comprise about 2 to about 5 arabinonucleotide or 2'-deoxyribonucleotides.

5. The oligonucleotide of claim 4, wherein said segments each independently comprise about 3 to about 4 arabinonucleotide or 2'-deoxyribonucleotides.

6. The oligonucleotide of claim 5, wherein said segments each independently comprise about 3 arabinonucleotide or 2'-deoxyribonucleotides.

7. The oligonucleotide of claim 1, wherein said oligonucleotide has a structure selected from the group consisting of:

| a) | $(A_x-D_y)_n$ | I |
| b) | $(D_y-A_x)_n$ | II |
| c) | $(A_x-D_y)_m-A_x-D_y-A_x$ | III |
| d) | $(D_y-A_x)_m-D_y-A_x-D_y$ | IV | wherein each of m, x and y are each independently an integer greater than or equal to 1, n is an integer greater than or equal to 2, A is an arabinonucleotide and D is a 2'-deoxyribonucleotide, wherein at least one instance of each of x and y is greater than or equal to 2.

8. The oligonucleotide of claim 1, wherein said arabinonucleotide comprises a 2' substituent selected from the group consisting of fluorine, hydroxyl, amino, cyano, azido, —CH═CH$_2$, —C≡CH, alkyl, functionalized alkyl, alkoxy and functionalized alkoxy groups.

9. The oligonucleotide of claim 8, wherein said alkyl group is a lower alkyl group.

10. The oligonucleotide of claim 9, wherein said lower alkyl group is selected from the group consisting of methyl, ethyl and propyl groups.

11. The oligonucleotide of claim 8, wherein said functionalized alkyl group is selected from the group consisting of methylamino, ethylamino and propylamino groups.

12. The oligonucleotide of claim 8, wherein said alkoxy group is selected from the group consisting of methoxy, ethoxy and propoxy groups.

13. The oligonucleotide of claim 8, wherein said functionalized alkoxy group is —O(CH$_2$)$_q$—R, wherein q=2, 3 or 4 and —R is selected from the group consisting of —NH$_2$, —OCH$_3$, and —OCH$_2$CH$_3$ groups.

14. The oligonucleotide of claim 7, wherein the arabinonucleotide is a 2'fluoroarabinonucleotide (2'F-ANA).

15. The oligonucleotide of claim 1, wherein said oligonucleotide consists of about 30 or fewer nucleotides.

16. The oligonucleotide of claim 15, wherein said oligonucleotide consists of about 8 to about 25 nucleotides.

17. The oligonucleotide of claim 16, wherein said oligonucleotide consists of about 18 nucleotides.

18. The oligonucleotide of claim 7, wherein said oligonucleotide has structure I wherein x=3, y=3 and n=3, thereby having a structure:

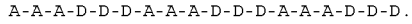

19. The oligonucleotide of claim 1, wherein said oligonucleotide is antisense to a target RNA.

20. A composition comprising the oligonucleotide according to claim 19 in admixture with a pharmaceutically acceptable carrier.

21. A commercial package comprising the oligonucleotide according to claim 19 together with instructions for its use.

22. The commercial package of claim 21, wherein said instructions are for a use selected from the group consisting of:
  a. inducing RNase H-mediated cleavage of a target RNA in a system;
  b. preventing or decreasing translation of a target RNA in a system;
  c. preventing or decreasing reverse transcription of a target RNA in a system;
  d. preventing or decreasing replication of a target RNA in a system;
  e. detecting the presence of a target RNA in a system;
  f. validating a gene target in a system;
  g. preventing or treating a disease related to a target RNA in a system; and
  h. any combination of a. to g.

23. The oligonucleotide of claim 7, wherein the arabinonucleotide has fluorine as a 2' substituent, and the oligonucleotide has structure (Ax-Dy)n.

* * * * *